US011155401B2

(12) United States Patent
Ray

(10) Patent No.: US 11,155,401 B2
(45) Date of Patent: Oct. 26, 2021

(54) SANITARY GLOVE DISPENSING APPARATUS

(71) Applicant: Ilya Ray, Trevor, WI (US)

(72) Inventor: Ilya Ray, Trevor, WI (US)

(*) Notice: Subject to any disclaimer, the term of this patent is extended or adjusted under 35 U.S.C. 154(b) by 0 days.

(21) Appl. No.: 15/015,304

(22) Filed: Feb. 4, 2016

(65) Prior Publication Data

US 2016/0152403 A1    Jun. 2, 2016

(51) Int. Cl.
*B65D 83/08* (2006.01)
*A61B 42/40* (2016.01)
*A61B 17/00* (2006.01)

(52) U.S. Cl.
CPC .......... *B65D 83/0894* (2013.01); *A61B 42/40* (2016.02); *B65D 83/0811* (2013.01); *A61B 2017/00889* (2013.01)

(58) Field of Classification Search
CPC . B65D 83/0894; B65D 83/0811; A61B 19/04; A61B 19/45; A61B 2019/4836; A61B 42/40; A61B 2017/00889
USPC ............................................... 221/38, 33, 45
See application file for complete search history.

(56) References Cited

U.S. PATENT DOCUMENTS

| | | | |
|---|---|---|---|
| 2,264,631 A | 12/1941 | Fetty | |
| 3,432,217 A | 3/1969 | Cowan | |
| 3,851,760 A * | 12/1974 | Smith | B65D 83/0805 206/390 |
| 4,034,853 A * | 7/1977 | Smith | B29C 66/43 206/278 |
| 4,108,513 A | 8/1978 | Lander | |
| 4,436,231 A * | 3/1984 | Kelly | A41D 19/043 223/40 |
| 4,771,966 A | 9/1988 | Anderson | |
| 4,773,532 A * | 9/1988 | Stephenson | B65D 83/0811 206/278 |
| 4,790,490 A | 12/1988 | Chakravorty | |
| 4,796,825 A | 1/1989 | Hawkins | |
| 4,826,262 A | 5/1989 | Hartman et al. | |
| 4,844,256 A * | 7/1989 | Honegger | B65B 25/148 206/390 |
| 4,863,064 A * | 9/1989 | Dailey, III | B65D 75/54 221/48 |

(Continued)

FOREIGN PATENT DOCUMENTS

WO    WO-2010086645 A1 *    8/2010    ............... B65D 5/10

OTHER PUBLICATIONS

Sep. 2014, "Norovirus Transmission Between Hands, Gloves, Utensils, and Fresh Produce During Simulated Food Handling," *Appl Environ Microbiol.*, Sep. 2014; 80(17): 5403-5410. doi: 10.1128/AEM.01162-14, M. Ronnqvist; E. Aho; A. Mikkela; J. Ranta; P. Tuominen; M. Rano and L. Maunula.

(Continued)

*Primary Examiner* — Rakesh Kumar

(74) *Attorney, Agent, or Firm* — Jansson Munger McKinley & Kirby Ltd.

(57) ABSTRACT

A sanitary glove dispensing apparatus. The sanitary glove dispensing apparatus, dispenses connected protective gloves overlapped in a pre-determined pattern, by both cuff ends, so that finger ends of the protective gloves are not contaminated during dispensing and protecting remaining protective gloves in the apparatus from surrounding environment and from other users of the apparatus.

8 Claims, 8 Drawing Sheets

10

FINGER END

12

14

CUFF END

16

(56) References Cited

U.S. PATENT DOCUMENTS

| | | | |
|---|---|---|---|
| D307,841 S | 5/1990 | Hanifl et al. | |
| 4,942,992 A | 7/1990 | Fischer et al. | |
| 4,960,248 A | 10/1990 | Bauer et al. | |
| 4,979,688 A | 12/1990 | Tinker | |
| 5,022,523 A * | 6/1991 | Honegger | B65H 29/006 206/390 |
| 5,050,737 A * | 9/1991 | Joslyn | B65D 77/0453 206/494 |
| 5,088,620 A | 2/1992 | Kelliher et al. | |
| 5,096,089 A * | 3/1992 | McLaughlin | B65D 83/0847 221/197 |
| 5,097,950 A | 3/1992 | Weiss et al. | |
| 5,101,610 A * | 4/1992 | Honegger | B65H 29/006 53/430 |
| 5,125,623 A | 6/1992 | Kiedinger | |
| 5,199,119 A | 4/1993 | Weber | |
| D335,373 S | 5/1993 | Mosior | |
| 5,329,672 A | 7/1994 | Froehlich et al. | |
| 5,361,812 A | 11/1994 | Arneson et al. | |
| 5,398,931 A | 3/1995 | Tahgoh | |
| 5,409,181 A | 4/1995 | Patrick | |
| 5,417,261 A | 5/1995 | Kanzler et al. | |
| 5,511,763 A | 4/1996 | Green | |
| 5,517,803 A * | 5/1996 | Stauber | B65B 63/04 206/390 |
| 5,520,308 A * | 5/1996 | Berg, Jr. | B65D 83/0894 221/50 |
| D375,010 S | 10/1996 | Karnes | |
| 5,562,229 A * | 10/1996 | Callahan | A47G 29/06 150/154 |
| 5,609,269 A * | 3/1997 | Behnke | B65D 83/0894 221/48 |
| 5,628,858 A * | 5/1997 | Petrou | B65C 1/00 156/247 |
| D385,626 S | 10/1997 | Mosior et al. | |
| D387,981 S | 12/1997 | Mosior et al. | |
| 5,695,065 A * | 12/1997 | Kennedy | B65D 33/001 206/494 |
| 5,772,291 A | 6/1998 | Byrd et al. | |
| 5,816,440 A * | 10/1998 | Shields | B65D 83/0805 221/45 |
| 5,878,909 A | 3/1999 | Rogow | |
| 5,884,784 A | 3/1999 | Betts, Sr. | |
| 5,921,434 A * | 7/1999 | Hollander | A61B 42/40 221/34 |
| 5,927,543 A | 7/1999 | Dejardin et al. | |
| 6,021,919 A * | 2/2000 | Kelly | A61B 42/40 221/155 |
| 6,021,920 A | 2/2000 | Aldape | |
| 6,062,421 A * | 5/2000 | Marley | A47F 1/04 221/45 |
| 6,098,917 A | 8/2000 | Cruz | |
| 6,112,936 A * | 9/2000 | Arizmendi | B65D 83/0805 150/154 |
| RE37,164 E * | 5/2001 | Petrou | B65C 1/00 156/247 |
| 6,286,712 B1 * | 9/2001 | Craig | B65H 45/24 206/494 |
| 6,305,572 B1 * | 10/2001 | Daniels | B65D 33/002 206/390 |
| 6,401,971 B1 * | 6/2002 | Edwards | B65D 5/5007 221/26 |
| D460,301 S | 7/2002 | Milliorn | |
| 6,488,175 B2 * | 12/2002 | Shiffler | B65D 83/0805 221/33 |
| 6,543,642 B1 * | 4/2003 | Milliorn | B65D 77/06 221/46 |
| 6,607,160 B2 | 8/2003 | Lewis et al. | |
| 6,708,841 B2 | 3/2004 | Baughman | |
| 6,749,148 B2 | 6/2004 | Helfer-Grand | |
| 6,820,753 B2 | 11/2004 | Kurtz et al. | |
| 6,901,723 B2 * | 6/2005 | Jordan | B65D 83/0805 221/38 |
| 6,903,654 B2 | 6/2005 | Hansen et al. | |
| 6,953,130 B2 | 10/2005 | Corbett | |
| 6,977,588 B2 | 12/2005 | Schotz | |
| 6,991,840 B2 * | 1/2006 | Sosalla | B65H 35/02 428/43 |
| 7,063,233 B2 * | 6/2006 | Jordan | B65D 83/0805 221/197 |
| D530,224 S | 10/2006 | Mattesky | |
| D540,082 S | 4/2007 | Mandel | |
| 7,296,765 B2 | 11/2007 | Rodrian | |
| 7,588,168 B2 | 9/2009 | Bagwell et al. | |
| 7,635,067 B1 | 12/2009 | Flynn | |
| 7,699,189 B2 * | 4/2010 | Tramontina | B65D 83/0817 221/36 |
| 7,703,647 B2 * | 4/2010 | Gochanour | A61B 42/40 225/90 |
| 7,731,056 B2 * | 6/2010 | Tramontina | A61B 50/10 221/36 |
| 7,841,556 B2 | 11/2010 | Elliott et al. | |
| 7,866,507 B2 * | 1/2011 | Sawin | B65D 25/205 222/1 |
| 7,963,475 B2 | 6/2011 | Rodrian | |
| 7,975,455 B1 * | 7/2011 | Abrahamsen | B65B 7/167 53/428 |
| 7,987,756 B2 | 8/2011 | Lewis et al. | |
| 8,061,558 B2 * | 11/2011 | Jordan | B65D 83/0894 221/197 |
| 8,132,692 B2 * | 3/2012 | Jordan | B65D 83/0805 221/197 |
| 8,196,775 B1 | 6/2012 | Ballesteros | |
| 8,237,558 B2 | 8/2012 | Seyed Momen et al. | |
| 8,419,024 B1 | 4/2013 | Arroyo-Ferrer | |
| 8,463,765 B2 | 6/2013 | Lesavich | |
| D696,107 S | 12/2013 | Kimple et al. | |
| 8,608,719 B2 | 12/2013 | Ray | |
| 8,617,130 B2 | 12/2013 | Ray | |
| 8,646,653 B2 * | 2/2014 | Lien | B65D 83/0805 221/305 |
| 8,684,226 B2 * | 4/2014 | Lien | B65D 83/0894 221/45 |
| D710,215 S * | 8/2014 | Palmer | D9/734 |
| 8,807,402 B2 * | 8/2014 | Backhaus | A41D 19/0072 223/111 |
| 8,960,493 B1 | 2/2015 | Dennison et al. | |
| 8,960,514 B2 | 2/2015 | Lee | |
| 9,037,564 B2 | 5/2015 | Lesavich et al. | |
| D732,305 S | 6/2015 | Cosentino | |
| 9,078,647 B2 | 7/2015 | Dennison et al. | |
| 9,095,299 B2 | 8/2015 | Ray | |
| 9,137,250 B2 | 9/2015 | Lesavich et al. | |
| 9,139,355 B2 * | 9/2015 | Yao | B65B 5/06 |
| 9,237,899 B2 | 1/2016 | Ray | |
| 10,053,278 B2 * | 8/2018 | Ma | B65D 83/08 |
| 2002/0040912 A1 * | 4/2002 | McHugh | A61B 50/30 221/45 |
| 2002/0113079 A1 | 8/2002 | Corbett | |
| 2003/0057222 A1 * | 3/2003 | Milliorn | B65D 77/06 221/46 |
| 2003/0116580 A1 * | 6/2003 | Baughman | A61B 42/40 221/45 |
| 2003/0222779 A1 | 12/2003 | Schotz et al. | |
| 2003/0230591 A1 | 12/2003 | Jordan et al. | |
| 2004/0099623 A1 * | 5/2004 | Kurtz | A47K 10/20 211/85.17 |
| 2004/0124202 A1 * | 7/2004 | Mitchell | B65H 1/04 221/34 |
| 2004/0134924 A1 | 7/2004 | Hansen et al. | |
| 2004/0172918 A1 * | 9/2004 | Jordan | A61B 42/40 53/429 |
| 2004/0245269 A1 * | 12/2004 | Grinberg | B65D 77/2024 221/38 |
| 2005/0015846 A1 * | 1/2005 | Vistins | B29C 41/14 2/161.7 |
| 2005/0271842 A1 * | 12/2005 | Triebes | A41D 19/0058 428/35.7 |
| 2006/0144847 A1 | 7/2006 | Jordan et al. | |
| 2006/0175341 A1 | 8/2006 | Rodrian | |

(56) References Cited

U.S. PATENT DOCUMENTS

| | | | |
|---|---|---|---|
| 2007/0010389 A1 | 1/2007 | Cutrona | |
| 2007/0012714 A1 | 1/2007 | Bagwell et al. | |
| 2007/0158359 A1 | 7/2007 | Rodrian | |
| 2007/0213877 A1 | 9/2007 | Hart et al. | |
| 2007/0215628 A1 | 9/2007 | Tramontina | |
| 2007/0222554 A1 | 9/2007 | Hart | |
| 2008/0011766 A1* | 1/2008 | Jordan | B65D 83/0894 221/45 |
| 2008/0061073 A1* | 3/2008 | Laroche | A47K 10/421 221/46 |
| 2008/0064278 A1* | 3/2008 | Oaroche | B65D 83/0805 442/59 |
| 2008/0105699 A1* | 5/2008 | Wong | A47K 10/42 221/47 |
| 2008/0116314 A1 | 5/2008 | Elliott | |
| 2008/0311409 A1* | 12/2008 | Lipinski | B29C 33/64 428/451 |
| 2009/0108122 A1 | 4/2009 | Sahud | |
| 2009/0140001 A1 | 6/2009 | Lewis | |
| 2009/0263440 A1* | 10/2009 | Kendall | A01N 25/34 424/412 |
| 2010/0102101 A1 | 4/2010 | Keily | |
| 2010/0117836 A1 | 5/2010 | Seyed Momen et al. | |
| 2011/0062179 A1* | 3/2011 | Stollery | A61B 42/40 221/45 |
| 2011/0108587 A1* | 5/2011 | Williams | A61B 42/40 223/111 |
| 2011/0208710 A1 | 8/2011 | Lesavich | |
| 2012/0199602 A1 | 8/2012 | Jordan et al. | |
| 2012/0278622 A1 | 11/2012 | Lesavich et al. | |
| 2014/0013484 A1* | 1/2014 | Bhalla | A41D 19/0044 2/161.6 |
| 2014/0061220 A1* | 3/2014 | Kowal | B65D 85/18 221/135 |
| 2014/0189792 A1 | 7/2014 | Lesavich et al. | |
| 2015/0053709 A1 | 2/2015 | Dennison et al. | |
| 2015/0053710 A1 | 2/2015 | Dennison et al. | |
| 2015/0230645 A1* | 8/2015 | Dennison | A61B 42/10 221/1 |
| 2015/0232216 A1* | 8/2015 | Stollery | B65B 25/20 53/436 |
| 2015/0374441 A1* | 12/2015 | Machado | A61B 50/20 221/2 |
| 2015/0379301 A1 | 12/2015 | Lesavich et al. | |
| 2016/0023838 A1* | 1/2016 | Chu | B65B 7/26 221/1 |
| 2016/0152403 A1* | 6/2016 | Ray | B65D 83/0894 221/1 |
| 2017/0370056 A1* | 12/2017 | McDonald | B65F 1/002 |
| 2018/0194539 A1* | 7/2018 | Ma | B65D 83/0088 |

OTHER PUBLICATIONS

Aug. 2009, "Norovirus on Swabs Taken from Hands Illustrate Route of Transmission: A Case Study," *J Food Prot.* Aug. 2009; 72(8):1753-5, L. Boxman; R. Dijkman; L. Verhoef; A. Maat; G. van Dijk; H. Vennema; M. Koopmans.

Aug. 2008, "Hand Washing Frequencies and Procedures Used in Retail Food Services," *J Food Prot.*, Aug. 2008, 71(8):1641-50, C. Strohbehn; J. Sneed; P. Paez; J. Meyer.

Mar. 1, 2015, "Systematic Qualitative Literature Review of Health Care Workers' Compliance with Hand Hygiene Guidelines," Mar. 1, 2015, vol. 43, Issue 3, pp. 269-274, Maura P. Smiddv, MPH; Rhona 0'Connell, PhD; Sile A. Creedon, PhD.

Jun. 6, 2014, "Vital Signs: Foodborne Norovirus Outbreaks—United States, 2009-2012," Jun. 6, 2014 / 63(22);491-495 Aron J. Hall, DVM; Mary E. Wikswo, MPH; Kimberly Pringle, MD; L. Hannah Gould, PhD; Umesh D. Parashar, MBBS.

Jan. 2005, "Preliminary Evaluation of the Effect of Glove Use by Food Handlers in Fast Food Restaurants," *Journal of Food Protection*, No. 1, Jan. 2005, pp. 4-207, pp. 187-190(4). Robert A. Lynch; Margaret L. Phillips; Brenda L. Elledge; Sridhar Hanumanthaiah; Daniel T. Boatright.

Jun. 2013, "Bacterial Contamination of Unused, Disposable Non-Sterile Gloves on a Hospital Orthopedic Ward," *Australas Med J.*, Jun. 30, 2013;6(6):331-8. doi: 10.4066/AMJ.2013.1675. Print 2013. Hughes KA; Cornwall J; Theis J-C; Brooks HJL.

Aug. 2009, "Glove Use Information Leaflet," World Health Organization, Aug. 2009, http://www.who.int/gpsc/5may/Glove_Use-Information_Leaflet.pdf.

Jun. 2008, "Identifying Specific Beliefs to Target to Improve Restaurant Employees' Intentions for Performing Three Important Food Safety Behaviors," *J Am Diet Assoc.*, Jun. 2008;108(6):991-7. doi: 10.1016/j.jada.2008.03.014, Valerie K. Pilling, PhD; Laura A. Brannon, PhD; Carol W. Shanklin, PhD, RD; Amber D. Howells, MS, RD; Kevin R. Roberts, PhD.

Nov. 2013, "Comprehensive Survey of Hand Hygiene Measurement and Improvement Practices in the Veterans Health Administration," *American Journal of Infection Control*, vol. 41, Issue 11, Nov. 2013, pp. 989-993. Heather Schacht Reisinger, PhD; Jun Yin, MS; Lewis Radonovich, MD; V. Troy Knighton, EdS; Richard A. Martinello, MD; Michael J. Hodgson, MD, MPH; Eli Perencevich, MD, MS.

Apr. 2006, "Bacterial Contamination of Nonsterile Disposable Gloves Before Use," *American Journal of Infection Control*, vol. 34, Issue 3, Apr. 2006, pp. 128-130, Philippe Berthelot, MD, MPH, PhD; Jonathan Dietemann, Pharm D; Pascal Fascia, MD; Alain Ros, MD; Franck Olivier Mallaval, MD; Frederic Lucht, MD; Bruno Pozzetto, MD, PhD, Florence Grattard, MD, PhD.

Aug. 2009, World Health Organization, Glove Use Information Leaflet, 4 pp.

\* cited by examiner

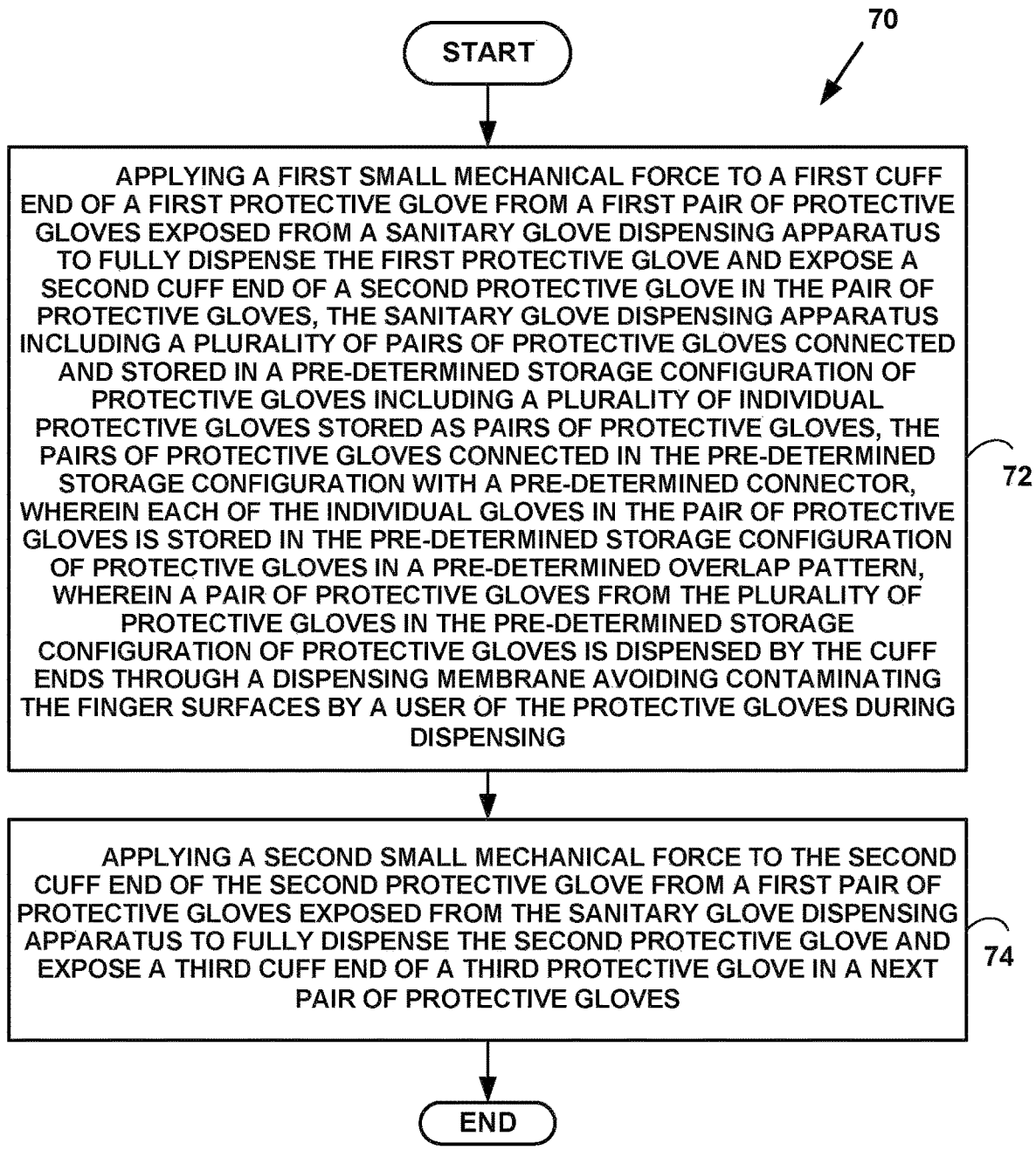

SANITARY GLOVE DISPENSING APPARATUS

FIELD OF INVENTION

This application relates to automatic dispensing of protective gloves. More specifically, it relates to a sanitary glove dispensing apparatus.

BACKGROUND OF THE INVENTION

Hand to person transfer of pathogenic organisms due to poor hand hygiene is a well-documented in the medical literature and results in thousands of deaths and hundreds of millions of dollars of health care expense each year. There are recognized problems associated with hand hygiene documented in hospitals, nursing homes, day-care facilities, dental offices, the food service industry, etc.

In 2005 the World Health Organization launched its first Global Patient Safety Challenge, focusing on the importance of hand hygiene. Hospital acquired infections occur in an estimated 5 to 10% of hospitalized patients and results in prolonged hospital stays, deaths and hundreds of millions of health care dollars each year. Proper hand hygiene has been recognized as the single most important element to control infection rates in all types of care facilities across all age groups. Multiple studies have shown that consistent hand washing or sanitizing hygiene compliance is low.

An important element of hand hygiene practice is the correct application of single use, non-sterile gloves, which can reduce the spread of pathogenic organisms. Unfortunately studies have demonstrated the presence of bacteria on unused gloves in open boxes, which are commonly used in all settings where non-sterile gloves are worn. Common skin bacteria and pathogenic bacteria were cultured from the glove surfaces, indicating that the non-sterile gloves may be a potential source of bacteria transmission in the health care setting. The method of boxing and retrieving the glove may be responsible for the contamination of the glove surface.

Norovirus is the leading cause of gastroenteritis and foodborne disease in the US, causing an estimated 56,000 to 71,000 hospitalizations and 570-800 deaths annually. Other recognized pathogens on food service personnel include *Staphylococcus aureus, Escherichia coli, Klebsiella* spp. and *coliform* bacteria. Transmission is mainly fecal-oral route. Up to 46% of gloved samples tested in one study in the fast food setting showed bacterial contamination and a separate study showed that norovirus contaminated gloves transmitted virus to food servings more readily than a contaminated cucumber. The observed tendency of food workers to wear gloves for an extended period of time has been felt to be one of the potential failure of gloves to reduce or prevent bacterial contamination.

The Food and Drug Association (FDA) 2001 Food Code, section 3-301.11 states, "Except when washing fruits and vegetables, food employees may not contact exposed ready to eat foods with their bare hands and should use suitable utensils . . . and single use gloves."

Regardless of the setting where non-sterile, one time use gloves are used there is a significant risk of contamination of the glove surface occurring when the glove is removed from a box or other dispenser.

There are a number of problems associated with protective gloves. One serious problem is that protective gloves are sold in paper boxes that are open on the top surface through a central oval shaped opening, the same configuration seen with tissue dispensers. When a glove is taken from the box it is grasped through the opening. Virtually all glove boxes present the glove so it is removed from the box by grasping the glove from the working surface that includes the base of the fingers and the palm. The cuff of the glove is not visible from most all glove boxes. It is common that more than one glove is grasped at a time so the gloves are held by the working surface until they can be put on. Often more than two gloves are grasped and the third or fourth glove removed from the box is pushed back into the box. The remaining gloves are now potentially contaminated by the person currently putting on the gloves and will receive further direct hand contact contamination by the next person removing a pair of gloves. Each pair of gloves removed from the open box, may have received surface contamination form two persons, prior to being used for direct patient care or food preparation.

Another problem that protective gloves are kept in open boxes on a wall dispenser or on a counter by the wash sink. Further contamination by bacteria and viruses from the surrounding environment is possible by air borne, respiratory born or splash contamination from the hand washing area which may include blood, tissue and other medical related fluids or food fluids or cleaning fluids, etc.

Another problem is that even for the most diligent and motivated health care workers, it is not possible to easily grasp gloves one at a time from the non-working surface. In the busy flow of a typical patient care unit gloves are grasped as one walks into the room and put on while moving toward the patient with the working surface of the glove coming into contact with bare hands. In those instances where hand hygiene is not performed according to accepted standards, patient to care giver to patient pathogen transmission is possible.

Another problem is that food industry studies have shown that hands or protective gloves contaminated with Norovirus can transmit virus to the working surface of other protective gloves and then to the food being handled.

Another problem is that different areas of food preparation require frequent glove changes, depending on the specific duty. Many of the individuals involved in the food service industry work part-time and may have limited levels of education. Understanding the importance of hand hygiene and glove wearing procedures are often discounted leading to poor compliance rates and increased risk of transmission of food borne pathogens.

Another problem is that ongoing monitoring and correcting non-compliant behavior requires direct observation and intervention, a process that is not practical on an ongoing basis in all lines of health and food service industries.

There have been attempts to solve some of the problems associated with dispensing gloves and protective gloves.

For example, U.S. Pat. No. 9,186,012, that issued to Rogers, et al. teaches "The glove dispensing device enables the placement of a glove on a glove retainer. The placement of the glove on the glove retainer at least partially seals the glove with the glove retainer. The user activates a vacuum that draws the glove into a housing of the glove dispensing device. The vacuum inverts the glove thus opening the glove to allow placement of the user's hand within the glove. The user may then remove his hand with the glove from the glove retainer. To assist with removing the glove from the glove retainer, the glove dispensing device provides a release toggle stored within the glove retainer. The user adjusts the release toggle to break the seal of the glove with the glove retainer. Breaking the seal overcomes the pressure applied to the glove from the vacuum. Thus, the glove is applied to the user's hand and ready for use."

U.S. Pat. No. 9,078,647, that issued to Dennison, et al., teaches A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, where the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove. Furthermore, a disposable glove dispensing system may comprise a pack of interconnected disposable gloves, and a glove dispenser comprising two glove hangers for hanging the pack of disposable gloves hang.

U.S. Pat. No. 9,003,314 that issued to Cohen teaches "A dispenser is disclosed for flat items such as disposable gloves that are contained within a dispensing bag that has an at least partially-open front side. The dispenser includes a base that has a rear wall and a pair of opposing side walls. A non-opaque cover with a dispensing aperture there through is pivotally fixed between each side wall and adapted to swing between an open and a closed position. At least one elastic cord is stretched between each side wall to urge the dispensing bag towards the cover when the cover is in the closed position and the dispensing bag is between the cover and the at least one elastic cord. The front side of the dispensing bag may be non-opaque and open at a dispensing bag aperture there through, a temporary adhesive being fixed proximate a periphery of the dispensing bag aperture."

U.S. Pat. No. 8,684,226, that issued to Lien teaches "A glove dispensing assembly includes a stack of interfolded gloves. In particular, the gloves are folded in an S-like arrangement including a first fold and a second fold. The finger portion of a leading glove is folded in between a cuff portion and an intermediate portion of a subsequent glove. The manner in which the gloves are folded allows for the gloves to be dispensed in a perpendicular direction or a lateral direction."

U.S. Pat. No. 8,132,692, that issued to Jordan teaches "A method of interfolding gloves including superposing finger portion of second glove adjacent finger portion of first glove, with second glove finger portion being disposed parallel and in a direction opposite the first glove finger portion, in a superjacent opposing relationship. First glove hand and cuff are lapped over second glove finger to create lapped, superjacent opposing fold. By repeatedly lapping previous glove hand over subsequent glove fingers, a glove bundle is formed. Folding can be longitudinal before lapped, superjacent opposing folding. Gloves are disposed in portable dispenser with lapped, superjacent folding and dispensing opening cooperating to dispense one glove, cuff first."

U.S. Pat. No. 8,061,558, that issued to Jordan, et al. teaches "gloves and dispensers for gloves are generally discussed herein with particular discussions extended to disposable gloves packaged in a disposable dispenser configured to engage with a carrier. Aspects of the glove assemblies provided herein include a dispenser case having a flange having locking tab for sliding engagement with a channel on the carrier. The dispenser case may be removed from the carrier and a new dispenser case engaged to the carrier."

U.S. Pat. No. 7,874,455, that issued to Jordan, et al. teaches "Gloves and dispensers for gloves are generally discussed herein with particular discussions extended to disposable gloves packaged in a disposable dispenser configured to engage with a carrier. Aspects of the glove assemblies provided herein include a dispenser case having a flange having locking tab for sliding engagement with a channel on the carrier. The dispenser case may be removed from the carrier and a new dispenser case engaged to the carrier."

U.S. Pat. No. 7,731,056, that issued to Tramontina teaches "A dispenser for dispensing gloves is provided which includes a housing having an exit port, the housing also formed to include a compartment which is configured to hold a plurality of gloves therein. The dispenser includes a glove pusher movably coupled to the housing. At least a portion of the glove pusher is configured to move within the compartment of the housing and push at least a portion of a glove disposed in the compartment through the exit port. A cartridge configured to be disposed into a compartment of a dispenser is disclosed. The cartridge is formed to permit a portion of a dispenser to move into the internal compartment of the cartridge to move at least one of the plurality of gloves at least partially through the at least one opening in the cartridge. A dispensing assembly also may include a stack of gloves or a cartridge containing a plurality of gloves. A method of using a glove dispenser is also provided."

U.S. Pat. No. 7,635,067, that issued to Flynn teaches "A glove dispensing system includes glove bearing sheets and a glove opening mechanism. In use, the glove dispensing system opens a cuff end of the gloves carried by the glove bearing sheets and presents the open gloves to a user. As such, the glove dispensing system provides the user with a substantially sterile glove in a manner that allows the user to easily don the gloves while limiting a risk of the user contaminating an exterior surface of the glove by touching with his hands or other body parts. In one arrangement, the gloves are integrally formed as part of the glove bearing sheets, such as by a heat-sealing process. The gloves can include coupling mechanism that secures the gloves to the glove bearing sheets and that allows ease of removal of the gloves from the glove bearing sheets after being donned by the user by a user."

U.S. Pat. No. 7,063,223, that issued to Jordan et al., teaches "A method of interfolding gloves including superposing finger portion of second glove adjacent finger portion of first glove, with second glove finger portion being disposed parallel and in a direction opposite the first glove finger portion, in a superjacent opposing relationship. First glove hand and cuff are lapped over second glove finger, to create lapped, superjacent opposing fold. By repeatedly lapping previous glove hand over subsequent glove fingers, a glove bundle is formed. Folding can be longitudinal before lapped, superjacent opposing folding. Gloves are disposed in portable dispenser with lapped, superjacent folding and dispensing opening cooperating to dispense one glove, cuff first."

U.S. Pat. No. 6,953,130, that issued to Corbett teaches "An Improved Glove Dispenser is disclosed. The disclosed dispenser will automatically open a pair of standard disposable gloves in response to a user request, preferably by voice. The dispenser further includes a shuttle assembly that will retrieve and position a pair of gloves for donning. The preferred dispenser will accept glove cartridges that can be loaded into the dispenser without being touched by the hands of the person installing the cartridges. In other embodiments of the disclosed dispenser, there is the capability to provide two or more different-sized or configured gloves for donning by users. The preferred dispenser further includes an embodiment whereby the gloves are inflated prior to being donned, in order to further assist the user in donning the gloves. The preferred dispenser further includes a glove donning rack assembly that has a unique glove release assembly for releasing gloves onto hands inserted into them when desired."

U.S. Pat. No. 6,820,753, that issued to Kurtz, et al. teaches "A disposable glove dispenser bracket includes a back panel with a magnetic pad attached thereto for supporting the dispenser and lateral side panels with flanges to grip and hold a glove dispenser box. A biasing spring maintains the glove dispenser box appropriately positioned within the dispenser bracket.

U.S. Pat. No. 6,708,841, that issued to Baughman teaches "Glove dispenser having a back plate, a cover, a angled rack for securing a pre-packaged box of gloves within the device at an angle with respect to the back plate, and an aperture in the cover through which gloves can be dispensed at an ergonomic angle."

U.S. Pat. No. 6,543,642, that issued to Milliorn teaches "The present invention is directed to a glove dispenser system that includes a reusable container and a disposable pouch containing stacked, partially folded gloves. The container is rigid and generally rectangular and has a lid and a bottom, spaced, parallel front and back walls, two spaced, parallel side walls and an opening in the lid. The pouch is generally rectangular shaped and it has a pair of spaced parallel extending faces yieldably connected to one another. One of the faces has an opening aligned with the opening in the lid of the container. The pouch contains a plurality of gloves in a stacked folded relationship with one another. The folded relationship being formed by a thumb of the glove being folded under a palm area of the glove and fingers of the glove being folded over the thumb and the palm area. The configuration of the pouch opening and the folded relationship of the gloves provides for the removal of one of the plurality of glove at a time during a dispensing procedure."

U.S. Pat. No. 6,375,034, that issued to Corbett teaches "An Improved Glove Dispenser is disclosed. Also disclosed is a device that permits a user to don gloves without first touching their exterior. The disclosed device includes a plurality of gloves attached by their cuffs to a filament, with the filament and cuffs being dispensed from an exchangeable glove cartridge. It is a further feature that the dispenser may be responsive to a user's voice. Furthermore, the invention provides a new method for donning gloves that will prevent user contamination of the gloves by touching the exterior of the gloves during the donning process."

U.S. Pat. No. 6,042,241, that issued to Marley teaches "A glove dispensing device comprising a cabinet which is designed to be permanently affixed to a wall for dispensing gloves from the glove boxes stored within the cabinet. The cabinet of the glove dispensing device includes a housing and a cover swingably mounted to the housing to allow glove boxes to be inserted into the housing. The cover is provided with a sliding window which opens to permit removal of one glove at a time while closing the sliding window protects the remaining gloves from contaminants and pollutants from the surrounding environment."

U.S. Pat. No. 6,053,380, that issued to Sherrod teaches "This invention is an electronically sanitized medical glove dispensing machine. Not only does the machine place the warm gloves on your hands, it also takes them off and disposes of them in a sanitary way, such as a biohazard bag. The apparatus works via a compressor and a circuit board, along with sensors, "gripper clips", small air hoses, latex gloves, and a stainless steel housing. The sanitized glove is inflated so the hand can be placed in the glove before usage. A hook grips the gloves after the medical worker is finished with them, removes them, and sanitizes them."

U.S. Pat. No. 6,021,920 that issued to Aldape teaches "Emergency and other personnel needing gloves can retrieve them easily for donning using a glove and hand protectant dispenser. The dispenser includes a backboard having at least one detachable glove dispenser member disposed proximate a first edge of the backboard; and at least one detachable hand protectant disposer proximate a second edge of the backboard."

U.S. Pat. No. 6,021,919, that issued to Kelly teaches "The present invention relates to an improved dispenser for sanitary gloves. The dispenser comprises a rectangular enclosure having a top, bottom, left and right side walls, front and back, for receiving individually packaged sanitary gloves. The front is permanently joined to the top, bottom, left and back, while the right side wall is pivotally attached to the bottom wall. The front contains an opening near the top for dispensing the sanitary gloves one at a time. A window near the bottom portion of the front is used to visually inspect the quantity of gloves remaining in the dispenser at any given time."

U.S. Pat. No. 5,966,741 that issued to Klecina teaches "The instant invention provides an article of manufacture that includes: a generally flat planar stacked pad of at least two contiguously supertransposed disposable plastic gloves, each having a generally straight perforated weakened tear line above and generally transverse to the wrist portion of each of the gloves; and, a heat fused portion of the pad substantially adjacent to the perforated weakened tear line opposite the gloves sufficient to produce a substantially rigid single layer of plastic. The substantially rigid single layer further includes: an arrangement for mounting the article on a surface selected from the group consisting of a hole formed through the substantially rigid single layer, double sided adhesive pads mounted on the substantially rigid single layer or the combination of a hole and double sided adhesive pads; and, a label including printed indicia affixed to it."

U.S. Pat. No. 5,921,534 that issued to Hollander et al. teaches "A dispenser for a stack of thin, disposable gloves wherein the gloves are placed within a box-like housing. Included within the housing is a biasing means which presses against the stack of gloves directly adjacent the access opening into the gloves. Each uppermost glove in the stack includes a spot of adhesive which is to connect with the directly underneath glove with this spot being located directly adjacent this access opening. Included within the box-like housing is a dispensing opening with the uppermost glove to partially protrude from this dispensing opening. The users hand is to be inserted into the glove with the glove then being extracted with the adhesive functioning to partially dispense the next glove in the stack of gloves and locate that in a position facilitating connection with a human hand."

U.S. Pat. No. 5,878,909, Rogow that issued to "A glove dispenser including a glove dispensing housing. Further provided is a plurality of rods extending between side faces of the housing. A pair of gloves are releasably coupled adjacent an opening thereof between each rod. Finally, a dispensing mechanism is situated within the housing for allowing the dispensing of the gloves."

U.S. Pat. No. 5,816,440, that issued to Shields, et al. teaches "Containers for sterile gloves having long cuffs folding over the palms, leaving the fingers exposed beyond, are disclosed such that, upon opening, only the crease of each long cuff/palm overfold can be manually grasped. In one preferred embodiment, sterile containers initially covered with removable film are designed with single openings covered by slit film to dispense multiple surgical or examination gloves. Inside the containers, the overfolded cuffs of successive gloves are folded under the flexed fingers of the first and every succeeding glove, such that the user can serially extract externally sterile gloves by grasping the crease of each long cuff/palm overfold. One bare hand grasps the crease to glove the other. Then, the ungloved hand grasps the crease of the next glove, such that the fingers of the gloved hand can be inserted under the cuff/palm overfold to glove the bare hand. As results, the external surfaces of each extracted glove are never touched by a bare finger or any other contaminated object before use on a patient. Such containers can dispense specified numbers of examination or surgical gloves. In another embodiment, multiple pairs of surgical or examination gloves, each pair with thumbs apposed toward the palms, can be dispensed with the palms touching in separate sterile envelopes, each of which unseals to expose only the creases of the cuff overfolds. Such sterile envelopes can be boxed separately or in rolls from which each package is easily separated."

U.S. Pat. No. 5,028,620, that issued to Kelliher, et al. teaches "A dispenser for gloves comprising a tubular body having a first end and a second end and having a spring disposed therein. The spring is secured to a moveable disc shaped member. A flexible mammillated shaped element having a first end and a second end is secured to the disc shaped member at the first end and secures a plurality of gloves therein. The second end of the mammillated member is secured to the second end of said tubular body. A top element which slideably fits over the second end of the tubular body has an opening therein and a diaphragm element having an aperture therein is secured over said opening. The spring urges the disc shaped member against the flexible mammillated shaped member containing the gloves allowing removal of one glove at a time from the aperture in the diaphragm element."

U.S. Pat. No. 4,992,942 that issued to Fischer, et al. teaches "A glove dispenser comprising a case and a clip fastened to the case. The case has an open position and a closed position. A belt loop is formed on the back surface of the case so as to allow the case to be attached to a belt. The clip is fastened to the case so as to receive the cuff of a glove. The case comprises a back panel, and a connector on the back panel for releasably affixing the front panel in close proximity to the back panel. The clip is interposed between the back panel and the front panel. The clip is a member having a first portion affixed to the case and a second portion in torsional abutment with the first portion. The front panel includes a pocket formed therein for the receipt of additional disposable gloves."

U.S. Pat. No. 4,844,293 that issued to McLaughlin teaches "A dispensing apparatus for disposable, thin plastic gloves is disclosed wherein said gloves may be retrieved by the user one at a time in a relatively simple manner. The apparatus comprises a box-like, generally rectangular enclosure for housing a removably mounted packet containing a plurality of the disposable gloves arranged in the packet in closely spaced, planar unfolded condition. The enclosure is provided with a front window or opening and a removable top cover or cap. The packet of gloves is loaded into the enclosure through a top opening and are disposed so that they may be removed, one at a time, through the front opening of the enclosure. The packet comprises a pair of faces yieldably connected to one another which have a configuration generally conforming to the shape of the gloves in an open palm and finger planar condition. The enclosure includes means to support the packet carrying the gloves in a parallel relationship with the gloves being biasly urged toward the front window to conveniently present the outermost glove to the user."

U.S. Published Patent Application No. 20150374441 that was published by Machado, et al. discloses "a glove dispenser has a housing having first and second opposed walls. A glove roll is disposed within the housing for carrying a roll of removable gloves. An electro-mechanical feed mechanism rotates the roll. One or more proximity sensors are positioned within the housing to detect a user's hand and activate rotation of the glove roll. Activators are located on the housing first and second wall which activate the roll to rotate to dispense a glove from the roll. A take-up roll can be provided for receiving roll material after the gloves are dispensed.

U.S. Published Patent Application Nos. 20150230645, 20150053710 and 20150053709 that were published by Dennison, et al. discloses "A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, where the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove. Furthermore, a disposable glove dispensing system may comprise a pack of interconnected disposable gloves, and a glove dispenser comprising two glove hangers for hanging the pack of disposable gloves hang."

U.S. Published Patent Application No. 20120199602 that was published by Jordan discloses "Gloves and dispensers for gloves are generally discussed herein with particular discussions extended to disposable gloves packaged in a disposable dispenser configured to engage with a holder. Aspects of the glove assemblies provided herein include a tray responsive to the number of gloves in the dispenser, movable in a vertical direction within the disposable dispenser towards the dispenser opening with its movement facilitated by a telescoping piston or other biasing members, such as a conical spring. The dispenser may be removed from the holder and a new dispenser engaged to the holder. Aspects of the present disclosure also include a disposable dispenser having a biasing member urging a tray in a vertical direction in response to the number of gloves in the dispenser."

U.S. Published Patent Application No. 20110062179 that was published by Stollery discloses "The present invention relates to the dispensing of gloves from a dispenser. The dispenser (1) comprises a container (2) and a plurality of disposable gloves. The container (2) has a plurality of faces (3, 4, 5), and each glove has a cuff portion (36) and a finger portion (34), the cuff portion having a cuff (40) and the gloves being stacked one on another with the cuffs of the gloves being aligned on one side (42) of the stack (20) of gloves held within the container (2). The container (2) has in use a dispensing aperture (24) in at least one face (3, 5) of the container through which gloves can be dispensed. The gloves are oriented in the container (2) so that the gloves are positioned for dispensing cuff-first through the aperture (24), and the finger portion (34) of each glove is folded back against the cuff portion (36) of the same glove to protect the finger portion from user contact and contamination during dispensing of the glove. The cuff portion has a cuff opening for receiving a user's hand, the cuff opening facing outwards with respect to the dispensing aperture."

However, these solutions still do not solve all of the problems associated with safe method for dispensing protective gloves without contaminating the protective gloves. Thus, it is desirable to solve some of the problems associated with protective glove dispensers.

SUMMARY OF THE INVENTION

In accordance with preferred embodiments of the present invention, some of the problems associated with dispensing protective gloves are overcome. A sanitary glove dispensing apparatus is presented.

The sanitary glove dispensing apparatus, dispenses connected protective gloves overlapped in a pre-determined pattern, by both cuff ends, so finger ends of the protective gloves are not contaminated during dispensing and protecting remaining protective gloves in the apparatus from surrounding environment and from other users of the apparatus.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 12 is a flow diagram illustrating a method of dispensing protective gloves by cuff ends by an exemplary protective glove dispensing apparatus;

DETAILED DESCRIPTION OF PREFERRED EMBODIMENTS

Figure 1:
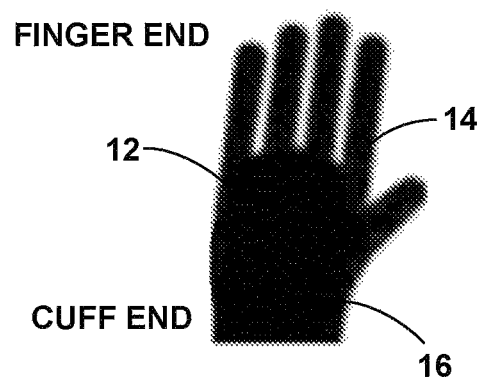
FIG. 1 is a block diagram illustrating an exemplary protective glove.

An important element of hand hygiene practice is the correct application of single use, non-sterile, or sterile protective gloves. The correct application can reduce the spread of pathogenic organisms. Unfortunately many studies have demonstrated the presence of bacteria and viruses on unused gloves in open boxes, non-automated and automated glove dispensers which are commonly used in all settings where non-sterile and sterile protective gloves are worn. The methods of boxing, dispensing and retrieving the protective gloves are responsible for the contamination of the glove surfaces including the finger ends and other surfaces of the gloves and lead to disease and infection outbreaks.

The World Health Organization (WHO) guidelines reflect current best practices for donning non-sterile gloves. The "Glove Use Information Leaflet," World Health Organization, August 2009, is incorporated herein by reference. For example, here is the WHO procedure for donning non-sterile examination gloves from a box of gloves: "(1) take a first single glove of out a box touching only a restricted surface of the first glove including a top edge of a first cuff of the glove; (2) don the first glove pulling the glove on the hand via the top edge of the cuff with the other hand; (3) take a second single glove by a top edge of a second cuff with the ungloved hand; (4) to avoid touching skin of hand or forearm of the ungloved hand, turn the external surface of the second glove to be donned on folded fingers of the gloved hand, thus permitting the second hand to be gloved; and (6) once gloved, the finger ends of the gloved hands should not touch any surface or thing not defined for use of the protective gloves."

Thus, it is desirable to provide and method and apparatus to dispense protective glove by cuff ends without contaminating surfaces of the protective gloves and without contaminating any other remaining gloves and/or without exposing any remaining protective gloves to a surrounding environment.

Protective Gloves-12

"Medical gloves" are disposable gloves used during medical examinations and procedures that help prevent contamination between caregivers and patients. Medical gloves are made of different polymers including latex, nitrile rubber, vinyl, neoprene and/or other materials. Medical gloves are typically 540 mils in thickness. A mil is a unit of length equal to one thousandth ($10^{-3}$) of an inch (0.0254 millimeters), used, for example, to specify the thickness of materials.

Medical gloves come unpowdered, or powdered with cornstarch or other powders to lubricate the gloves, making them easier to put on the hands. Unpowdered gloves are being used more often during surgery and other sensitive procedures. Special manufacturing processes are used to compensate for the lack of powder.

There are two main types of gloves: "exam" and "surgical." Surgical gloves have more precise sizing with a better precision and sensitivity and are made to a higher standard. Exam gloves are available as either sterile or non-sterile, while surgical gloves are generally sterile. Sterile gloves are free from bacteria or other living microorganisms.

Food service protective gloves and/or other types of protective gloves provide a cost-effective solution general food service applications to ensure food safety protection.

"Latex" is a stable dispersion emulsion of polymer microparticles in an aqueous medium. Latex itself is natural, but synthetic latexes have been made. Synthetic latexes can be made by polymerizing a monomer such asstyrene that has been emulsified with surfactants. Many people are allergic to latex and latex gloves cannot be used in such circumstances.

"Nitrile rubber," also known as Buna-N, Perbunan, acrylonitrile butadiene rubber, and NBR, is a synthetic rubber copolymer of acrylonitrile (ACN) and butadiene. Trade names include Nipol, Krynac and Europrene. Nitrile butadiene rubber (NBR) is a family of unsaturated copolymers of 2-propenenitrile and various butadiene monomers (1,2-butadiene and 1,3-butadiene). Although its physical and chemical properties vary depending on the polymer's composition of nitrile, this form of synthetic rubber is unusual in being generally resistant to oil, fuel, and other chemicals (the more nitrile within the polymer, the higher the resistance to oils but the lower the flexibility of the material).

"Neoprene" or polychloroprene is a family of synthetic rubbers that are produced by polymerization of chloroprene. Neoprene exhibits good chemical stability and maintains flexibility over a wide temperature range. Neoprene is sold either as solid rubber or in latex form.

"Vinyl" or ethenyl is the ethylene molecule minus one hydrogen atom. When used as medical gloves, due to vinyl gloves having less flexibility and elasticity, several guidelines recommend either latex or nitrile gloves for clinical care and procedures that require manual dexterity and/or that involve patient contact for more than a brief period.

"Polyethylene" (abbreviated PE) or polyethene is a common plastic. Food handler gloves made typically from PE are non-sterile and about one to five mils thickness.

However, the present invention is not limited to the specific types of protective gloves 20, 20' described and more, fewer and other types of protective gloves made from other types of materials can be used to practice the invention.

FIG. 1 is a block diagram 10 illustrating an exemplary protective glove 12. The protective glove 12 includes a finger end 14 and a cuff end 16.

Figure 2:
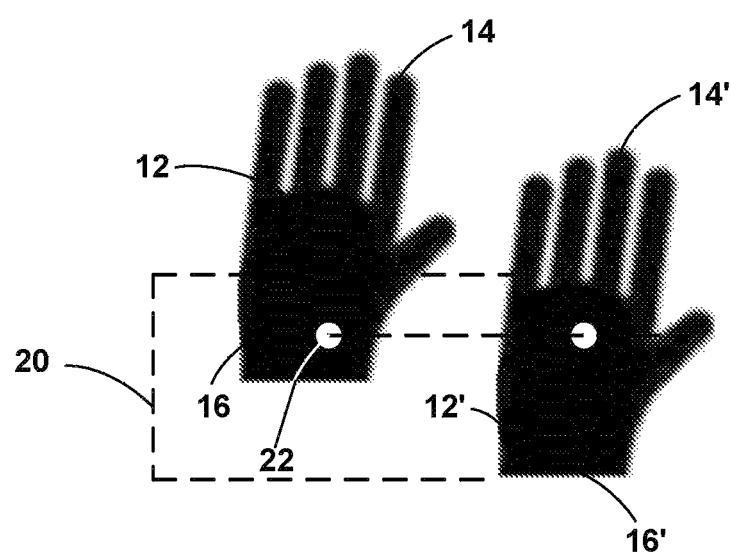
FIG. 2 is a block diagram illustrating an exploded view of an exemplary dispensing overlap for protective gloves.

FIG. 2 is a block diagram illustrating an exploded view of an exemplary pre-determined dispensing overlap distance 20 for protective gloves 12, 12' that are stored in a stack of gloves 36. Protective gloves 12, 12' are connected with a pre-determined mechanical connector 22.

In one embodiment, the pre-determined connector 22 is used to physically connect protective gloves 12, 12' for dispensing by the cuff ends 16, 16'. Protective gloves 12, 12' are properly dispensed by the cuff ends 16, 16' avoiding contamination of the finger ends 14, 14'.

In an exemplary embodiment, where the pre-determined connector 22 is used, the pre-determined connector 22 includes a connection created by a mechanical connector, by a chemical bond, a heat bond and/or a mechanical compression bond. However, the present invention is not limited to these connectors 22 and more, fewer or other connectors can also be used to practice the invention.

The mechanical connector 22 includes a small piece of tape or paper, plastic or other material and/or a grasping tab 28 with an applied pressure sensitive adhesive (PSA) as described herein. The tape includes medical tape, painters tape, cellophane tape or other type of tape depending on the type of protective gloves being used.

When protective gloves 12, 12' are dispensed, the tape can be used as a manual method to track how many gloves are dispensed by users 58. For example, each time protective gloves 12, 12' are dispensed by user 58, the user can place the piece of tape on a wall chart under his name next to a timeline indicating a time when the gloves where changed.

However, the tape connector 22 is not as desirable in a food service environment without care so the tape connector 22 does not end up in any food being served. It is also not as desirable in some medical environments such as surgical environments so the tape does not end up in any patients being operating on, etc.

The chemical connector 22 includes plural types of adhesives, rubber cement and/or other type of glues and/or adhesives that create a temporary chemical bond but does not affect use of the protective gloves 12, 12' in any environment that the protective gloves 12, 12' are used in. In one embodiment, the chemical connector 32 includes a pressure sensitive adhesive (PSA).

In one exemplary embodiment, the chemical connector 22 includes a "pressure-sensitive adhesive" (also called a self-adhesive, self-stick adhesive). A PSA is an adhesive which forms a bond when pressure is applied to marry an adhesive with au adhered surface. No solvent, water, or heat is needed to activate the adhesive. PSA are used in pressure-sensitive tapes, labels, note pads, and a wide variety of other products. A common example of a PSA is that used on the sticky-notes such as POST-IT notes.

PSAs are known and commonly used on medical applications such as contact wound care dressings, EKG electrode pads, medical tapes, analgesic and transdermal drug patches, and other medical applications.

Pressure-sensitive adhesives are designed with a balance between flow and resistance to flow. The bond forms because the adhesive is soft enough to flow, or wet, the "adherend." The bond has strength because the adhesive is hard enough to resist flow when stress is applied to the bond. Once the adhesive and the adherend are in proximity, there are also molecular interactions such as van der Waals forces involved in the bond, which contribute significantly to the ultimate bond strength. PSAs exhibit viscoelastic (viscous and elastic) properties, both of which are used for proper bonding.

Pressure-sensitive adhesives are characterized by their shear and peel resistance as well as their initial tack. These properties are dependent, among other things, on the formulation, coating thickness and temperature.

PSAs are usually based on an elastomer compounded with a suitable tackifier such as a rosin ester. An "elastomer" is a polymer with viscoelasticity (having both viscosity and elasticity) and very weak inter-molecular forces, generally having low Young's modulus and high failure strain compared with other materials. "Esters" are derived from an acid (e.g., Carbolic acid, etc.) and an alcohol. The elastomers include, but are not limited to, Butyl rubber Ethylene-vinyl acetate (EVA), Natural rubber, nitriles, Silicone rubbers. Styrene block copolymers (SBC) and/or Vinyl ethers. However, the present invention is not limited to these elastomers and other compounds for PSAs can be used to practice the invention.

None of the PSA's or other adhesives and/or glues used with the invention are harmful or detrimental to the user 58 of the protective gloves 12, 12' or anything the user 58 is using the gloves 12, 12' on or for surgical patient, etc.).

All of the bonds produced by the various types of PSA based bonding for the chemical connectors 22 are easily broken by a small mechanical force 62 applied to gloves 12, 12', such as downward force 62 by pulling the cuff end 16 of the first protective glove 12 in a downward motion and detaching it from the second protective glove 12' in the pair of bonded protective gloves as well as moving the second protective glove 12' out of the apparatus 40, 40' far enough for dispensing as well.

In one exemplary embodiment, a heat connector 22 includes heat bonding of protective gloves 12, 12'. The heat bonding includes, but is not limited to such methods as radiant heat bonding, point-bonding, ultrasonic boning, and/or other heat-based bonding techniques.

"Radiant heat bonding" takes place by exposing the protective gloves to a source of radiant energy in the infrared range. The electromagnetic energy radiated from the source is absorbed by the protective gloves 12, 12', increasing their temperature. The application of radiant heat is controlled so that it melts a small portion of the protective gloves 12, 12' material without affecting the rest of the glove surface. Bonding occurs when the glove material re-solidifies upon removal of the source of radiant heat.

"Point-bonding" is a method for thermally bonding in disposables as diaper, sanitary products, and medical products. This method involves the use of a two-roll nip consisting of a heated male patterned metal roll and a smooth or patterned metal roll. This second roll may or may not be heated, depending on the application. In a typical production line, each of gloves 12, 12' is fed by an apron leading to a calender nip and the glove material temperature is raised to the point at which tackiness and melting cause glove material segments caught between the tips of engraved points and the smooth roll to adhere together. A "calender" is a series of hard pressure rollers used to form or smooth a sheet of material such as paper or plastic film or protective gloves 12. The heating time is typically of the order of milliseconds. The bond breaking strength is dependent on the process temperature and pressure and other parameters like the contact time, quench rate and calender pattern.

"Ultrasonic bonding" is a process that involves the application of rapidly alternating compressive forces of ultrasonic vibrations to localized areas of the protective glove materials. The stress created by these compressive forces is converted to thermal energy, which softens the protective glove materials as they are pressed against each other. Upon removal from the source of ultrasonic vibration, the softened glove materials cool, solidifying the bond points. This method is frequently used for spot or patterned bonding of mechanically bonded materials. No binder is necessary when synthetic materials are used since these materials are self-bonding.

All of the bonds produced by the various types of heat based bonding are easily broken by a small mechanical force 62 applied to the pair of gloves, such as downward force by pulling the cuff end 16 of the first protective glove 12 in a downward motion and detaching it from the second protective glove 12' in the pair or bonded protective gloves.

In one exemplary embodiment, the mechanical connector 22 includes mechanical compression bonds created by running each pair of protective gloves through a die that presses or rolls a small portion of protective gloves 12, 12' together under high pressure.

All of the bonds produced by the various types of mechanical based bonding are easily broken by a small mechanical force applied to the gloves, such as downward force by pulling the cuff end 16 of the first protective glove 12 in a downward motion and detaching it from the second protective glove 12' in the pair of bonded protective gloves.

Figure 3:
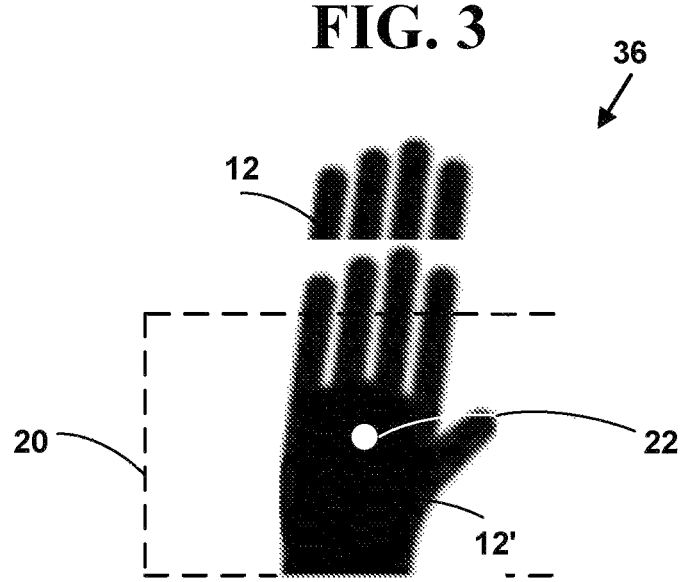
FIG. 3 is a block diagram illustrating a non-exploded view of an exemplary dispensing overlap for protective gloves.

FIG. 3 is a block diagram illustrating a non-exploded view of exemplary pre-determined dispensing overlap distance 20 for protective gloves 12, 12' that are stored in a chain 34 and/or stack of gloves 36.

The pre-determined dispensing overlap distance 20 includes overlapping a finger end 14" of a second glove 12' a pre-determined distance 20 over a palm, finger 14 and cuff end 16 of a first glove 12 in each pair of protective gloves 12, 12'. It has been determined experimentally that the optimal pre-determined overlap distance is about four inches (about ten centimeters) for the overlap distance to effectively dispense protective gloves 12, 12' by the cuff ends 16, 16'.

Figure 4:
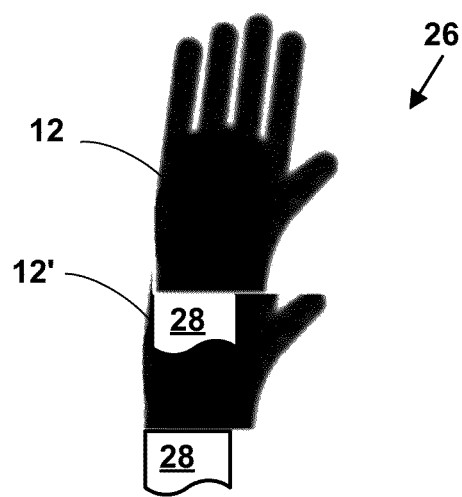
FIG. 4 is a block diagram illustrating an exemplary dispensing overlap for protective gloves.

FIG. 4 is a block diagram 26 illustrating an exemplary dispensing overlap for protective gloves 12, 12' with additional grasping tab 28.

In one embodiment of the invention, each protective glove 12 further includes an additional grasping tab 28 (FIG. 4) on the cuff end 16, 16' of each pair protective gloves 12, 12'. In one embodiment, the grasping tab 28 is added to a protective glove 12, 12' during a manufacturing process and is an integral part of the gloves 12, 12'. In such an embodiment, the grasping tabs 28 are used to grasp protective gloves 12, 12' so not even the cuff ends 16, 16' of the protective gloves 12, 12' are touched by a user when the gloves 12, 12' are dispensed from the apparatus 40, 40'.

In another embodiment, the grasping tab 28 is an additional type of mechanical connector 22 that is added after the gloves 12, 12' are manufactured (e.g., with a PSA, etc.)

In another embodiment, the grasping tab 28 includes an antimicrobial compound. However, the present invention is not limited to these embodiments and the invention can be practiced without using the additional grasping tab 28 on the protective gloves 12, 12'.

In one embodiment, the pre-determined connector 22 is not used at all. Instead the additional grasping tab on the cuff end 16, 16' of each pair protective gloves 12, 12' is used instead to connect protective gloves 12, 12'. The additional grasping tab may also include a chemical (e.g., PSA, etc.) or mechanical bond to keep protective gloves 12, 12' protected.

Protective gloves 12, 12' are illustrated as being connected with additional grasping tab. Various combinations of protective gloves 12, 12' can be used to practice the invention and gloves 12, 12' with and/or without connector 22 and/or with and without additional grasping tab can be mixed in a chain 34 or stack 36 of protective gloves.

Figure 5:
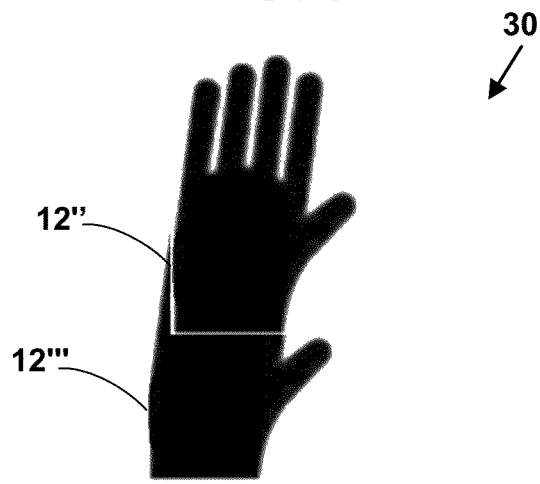
FIG. 5 is a block diagram illustrating an exemplary dispensing overlap for protective gloves.

FIG. 5 is a block diagram 30 illustrating an exemplary dispensing overlap for protective gloves 12", 12"'.

In one embodiment, the pre-determined connector 22 is not used at all to physically connect protective gloves 12", 12"'. In such an embodiment, protective gloves 12, 12' are kept together with friction forces caused by the pre-determined overlap distance 20 of protective gloves 12, 12'.

A friction force is a force exerted by a surface when an object moves across it (e.g., kinetic friction) or makes an effort to move across it (e.g., static friction). A "coefficient or friction" is a ratio between a force necessary to move one surface horizontally over another and the pressure between the two surfaces.

Protective gloves made of the various materials described herein have coefficient of frictions large enough to prevent protection gloves 12, 12' from becoming separated when stacked into a chain 34 or stack 36 of protective gloves 12, 12'. For example, the static coefficient of friction for surfaces of latex gloves known in the art range from about 0.38 for the donning surface (e.g., cuff end 16, 16') to about 1.17 for the gripping surfaces (i.e., fingers 14, 14", palm, etc.). In comparison, the coefficient of static friction for sandpaper on cardboard is about 0.81. So there is more than enough friction from the overlap of the protective gloves to keep the gloves together for dispensing by the cuff ends.

Figure 6:
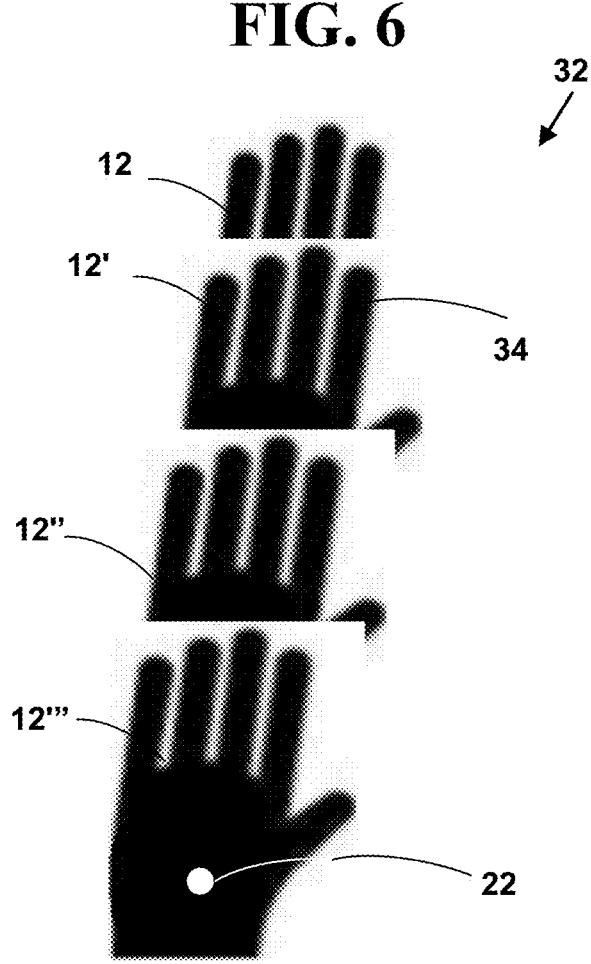
FIG. 6 is a block diagram illustrating an exemplary chain of protective gloves.

FIG. 6 is a block diagram 32 illustrating a top view of an exemplary chain 34 of protective gloves 12, 12', 12", 12"' overlapped 24 and connected with pre-determined connector 22. The gloves 12 in the chain 34 are illustrated with optimal overlap distance 20 adjusted to allow easier viewing of the features of the invention in the drawings.

The chain 34 of protective gloves 12, 12', 12", 12"' allows protective gloves 12, 12' to be dispensed by the cuff ends 16, 16' and also allows a cuff end 16" of a next glove 12" in a next protective glove 12,", 12" to be partially exposed to allow dispensing of the next protective glove 12", 12'".

In this embodiment, the chain 34 of protective gloves 12, 12', 12", 12'" allows protective gloves 12, 12' to be dispensed by cuff ends 16, 16', 16", 16'" from glove dispensing apparatus 40,40' to prevent contamination of the finger ends 14, 14', 14", 14'" of the protective gloves.

The stack 36 of protective gloves 12 includes pre-determined connectors 22 connecting protective gloves 12, 12' and 12', 12". In this embodiment, the pre-determined connectors 22 (e.g., PSA, bonding, tape, grasping tab 28, etc.) used between each of protective gloves 12, 12', 12', 12'" allow protective gloves 12, 12' to be dispensed by the cuff ends 16, 16' and also allow a cuff end 16" of a next glove 12" be partially exposed to allow dispensing of the next protective glove 12", 12".

In this embodiment, the stack 36 of protective gloves 12, 12', 12", 12'" allows protective gloves 12, 12' to be dispensed by cuff ends 16, 16', 16", 16'" from glove dispensing apparatus 40,40' to prevent contamination of the finger ends 14, 14', 14", 14'" of the protective gloves.

In another embodiment, the stack 36 of protective gloves 12 does not include any mechanical connectors 22. In such an embodiment, frictional forces allow proper dispensing of the protective gloves 12 by the cuff ends 16.

In one embodiment, the chains 34 or stacks 36 of protective gloves are attached to a paper and/or plastic and/or other material. However, this embodiment is less preferred because the attachment paper, etc. material generates significant amounts of additional waste that must be discarded and also adds additional cost to each chain 34 or stack 36 of protective gloves.

In one embodiment, the chains 34 and/or stacks 36 of protective gloves 12 include a protective cover (e.g., cellophane, vinyl, PVC, etc.) that protects the gloves 12 and is removed before installing into glove dispensing apparatus 40, 40'. The chains 34 and/or stacks 36 may also include a paper leader and/or plastic leader and/or leader made of another materials that is fed through a dispensing slot 44 for dispensing the protective gloves 12, 12' by cuff ends 16, 16". The paper leader is discarded after it is fed through dispensing slot 44 leaving the protective gloves 12, 12' connected together on the roll for dispensing from the glove dispensing apparatus 40, 40'.

In drawings, the dispensing slot 44 is illustrated as a rectangular shaped dispensing slot. However, the present invention is not limited to this embodiment and other shapes can be used for the dispensing slot 44 to practice the invention.

However, the present invention is not limited to the embodiments described and other embodiments can be used to practice the invention.

Exemplary Protective Glove Dispensing Apparatus-40

Figure 8:
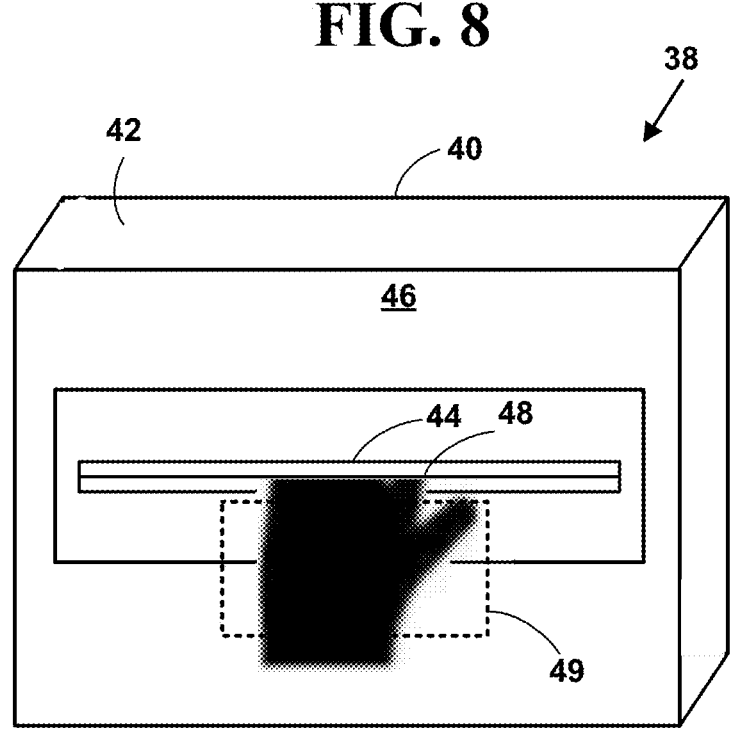
FIG. 8 is a block diagram illustrating a side view of an exemplary protective glove dispensing apparatus.

FIG. 8 is a block diagram 38 illustrating an exemplary side view of a protective glove dispensing apparatus 40 (not drawn to scale).

Figure 9:
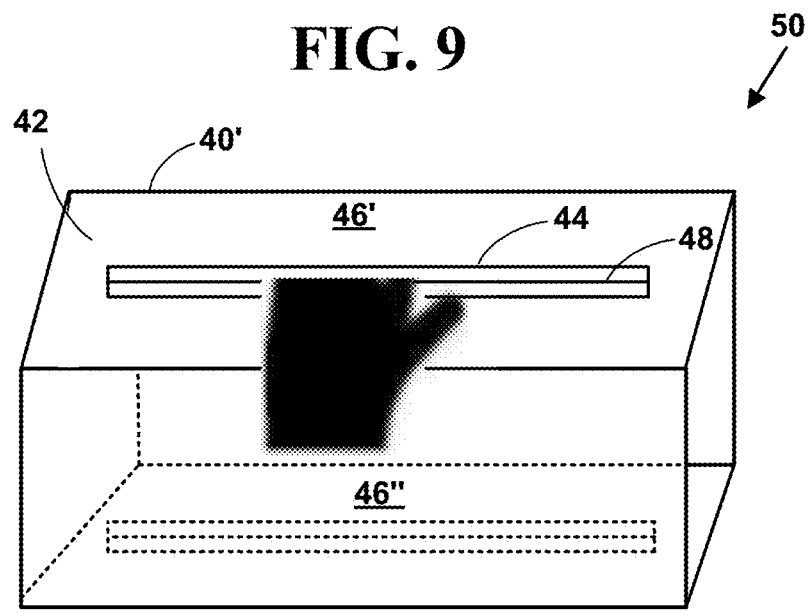
FIG. 9 is a block diagram illustrating a top view of an exemplary protective glove dispensing apparatus.

FIG. 9 is a block diagram 50 illustrating an exemplary side view of a protective glove dispensing apparatus 40' (not drawn to scale).

In FIG. 8, the glove apparatus 40 includes a protective case 42; a dispensing slot 44 in a surface 46 of the protective case 42 for dispensing protective gloves 12, 12' by cuff ends 16, 16'; a dispensing membrane 48 integral to the dispensing slot 44 with a membrane material with a pre-determined coefficient of friction value to separate a first protective glove 12 and expose a cuff end of a second protective glove 12' in protective gloves 12, 12', and to expose a cuff end 16" of a next of protective gloves 12", 12'" for dispensing when one or more small mechanical forces are applied to a cuff end 16 of a protective glove 12; protective gloves 12 connected and stored in a predetermined storage configuration protective gloves connected in the chain 34 with a pre-determined connector, wherein each of the individual gloves 12, 12' is stored in the pre-determined storage configuration of protective gloves in a pre-determined overlap pattern 20, wherein protective gloves 12, 12' from the plural protective gloves 12 in the pre-determined storage configuration of protective gloves is dispensed from the chain 34 of protective gloves by the cuff ends 16, 16' through the dispensing membrane 48 avoiding contaminating the finger surfaces 14, 14' by a user of the protective gloves 12 during dispensing.

However, the present invention is not limited to this embodiment and more, fewer or other components in the glove dispensing apparatus can also be used to practice the invention.

In one embodiment, the protective case 42 includes a paper, cardboard, plastic and/or other material. In such an embodiment, the protective case 42 is made from a disposable material. However, the present invention is not limited to these embodiments and other embodiments can also be used to practice the invention.

In another embodiment, the protective case 42 is made from a non-disposable material that is re-usable and re-fillable with new chains 34 and/or stacks 36 and/or other configurations of protective gloves 12. However, the present invention is not limited to these embodiments and other embodiments can also be used to practice the invention.

In a preferred embodiment, the protective case 42 is specifically sized and shaped to conform to existing size boxes of protective gloves.

For example, the protective case 42 is a rectangular box about three inches in depth, about five inches in width and about ten inches in length (e.g., about seven centimeters by about 12 centimeters by about twenty-five centimeters, etc.). The about three inch depth allows one hundred total protective gloves 12 to be stored in such a standardized box. Standard size boxes of protective gloves known in the art typically include one hundred protective gloves stored in a random clump within the confines of the box and are dispensed through an oval or circular shaped perforated hole in the box and do not include a dispensing membrane.

In the present invention, the standardized size of the protective case allows the protective case 42 including the protective gloves to be easily inserted into virtually all existing glove racks already known in the prior art for holding prior art boxes of protective gloves.

However, the present invention is not limited to these embodiments and other standard, non-standard sized and shaped embodiments can also be used to practice the invention.

In one embodiment, the dispensing slot 44 is included in a side surface 46 of the protective case 42 (FIG. 8). In this embodiment, it has been determined experimentally that including the dispensing slot 44 at about a mid-point in a side surface of the protective case 42 allows all of the gloves 12, 12' in the chain 34 of protective gloves 12 to be efficiently dispensed without use of a spring and/or other internal pressure mechanism that would push remaining gloves 12 in the chain 34 up and towards the dispensing slot 44. However, the present invention is not limited to this embodiment and other embodiments can also be used to practice the invention with the dispensing slot 44 in another surface of the protective case and without and/or with a spring and/or other internal pressure mechanism.

In another embodiment, the dispensing slot 44 of the glove dispensing apparatus 40' is included in a top surface 46' (FIG. 9). However, the present invention is not limited to this embodiment and other embodiments can also be used to practice the invention.

In another embodiment, the dispensing slot 44 is included in a bottom surface 46" (FIG. 9) In such an embodiment, the apparatus 40, 40' can be used in existing glove dispensing apparatus that allow protective gloves to be dispensed downward. However, the present invention is not limited to this embodiment and other embodiments can also be used to practice the invention.

In one embodiment, the dispensing membrane 48 is integral to the dispensing slot 44 for protecting protective gloves 12, 12' during dispensing and for protecting the plural protective gloves 12 in the chain 34 of protective gloves 12 from contamination includes an antimicrobial surface with an antimicrobial agent that inhibits or reduces the ability of microorganisms to grow on the surface of the dispensing membrane 46. The antimicrobial agents, include, but are not limited to, antibacterial, antifungal, antiviral and/or other antimicrobial agents.

In another embodiment, the dispensing membrane 48 coats each of protective gloves 12, 12' as they are dispensed from the gloved dispensing apparatus 40 with an antimicrobial agent. In such an embodiment, the dispensing membrane 48 includes an antimicrobial gel and/or other antimicrobial coating that is transferred from the dispensing membrane 48 onto each of protective gloves 12, 12' as they are dispensed for additional anti-contamination protection. However, the present invention is not limited to these embodiments and the invention can be practiced with and/or without any antimicrobial surfaces.

In one embodiment, the apparatus 40, if it includes a protective case 42 made out of a durable material such as plastic, rubber, composite materials, etc. further includes a dispensing membrane 48 that is replaceable, selectively removable and attachable and is replaced every time a new chain 34 of protective gloves is added to glove dispensing apparatus 40 to ensure the protective gloves 12 are not contaminated by an environment and/or user 58 the glove dispensing apparatus 40 is being operated in as the protective gloves 12, 12' are dispensed.

However, the present invention is not limited to these embodiments and other embodiments can be used to practice the invention.

In one embodiment, the pre-determined storage configuration of protective gloves includes a plurality of protective gloves 12, 12' stored in a chain 34 (FIG. 6) stack 36 (FIG. 8) or on a roll 68 (FIG. 7) of protective gloves 12, 12' for dispensing protective gloves 12, 12' by cuff ends 16, 16'.

However, the present invention is not limited to these embodiments and other embodiments and other storage configurations can be used to practice the invention.

In one embodiment, the chain 34 of protective gloves 12 is folded in a pre-determined manner to fit within the protective case 42 to allow easy dispensing by the cuff ends 16.

In one embodiment, the chain 34 of protective gloves is folded in a zig-zag pattern. A cuff end 16 of a first protective glove 12 extends from the dispensing slot 44. The first protective glove 12 overlaps (FIGS. 3-5) the second protective glove 12' with the pre-determined distance 20. However, the present invention is not limited to this embodiment and other folding patterns and other embodiments can be used to practice the invention.

In one embodiment, the connectors 22, 22' are a same connector. In another embodiment, the connectors 22, 22' are different connectors.

Figure 10:
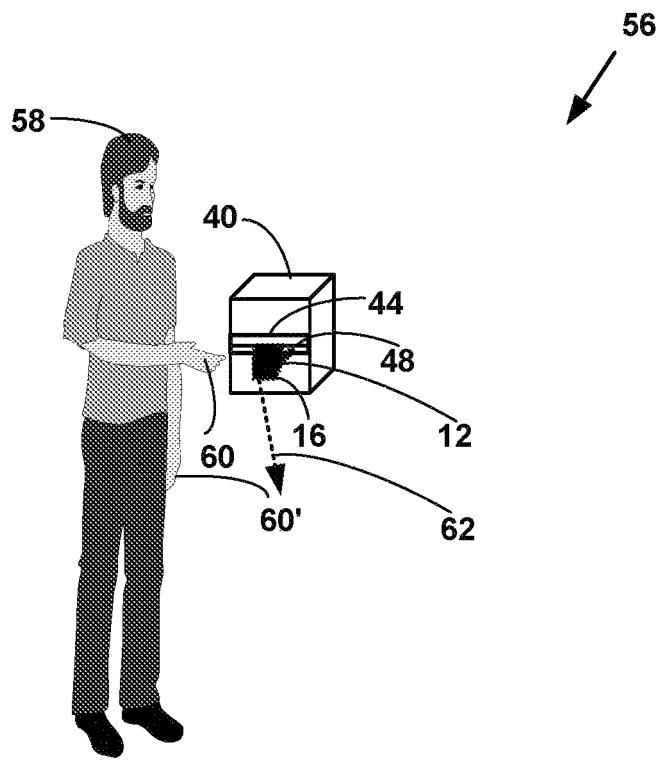
FIG. 10 is a block diagram illustrating an exemplary user of an exemplary protective glove dispensing apparatus.

FIG. 10 is a block diagram 56 illustrating an exemplary user 58 of an exemplary protective glove dispensing apparatus 40 (not drawn to scale) with the dispensing slot 44 on a side surface 46 (e.g., FIG. 8).

To dispense protective gloves, a user 58 tugs with the first hand 60 (or both hands 60, 60', etc.) on the exposed first cuff end 16 of the first glove 12 with a small mechanical force 62 such as a small mechanical force 62 of about five pounds of force or about 22.2 Newtons (N), etc. However, the present invention is not limited to such forces and other mechanical forces can be used to practice the invention.

In the United States, the small mechanical force 62 includes about five pounds or 22.2N force that is a maximum force an apparatus 40 can require for user actions and still be compliant for use under the Americans with Disabilities Act (ADA) (e.g., 42 U.S.C. ch. 126, § 12101 et seq.). However, the present invention is not limited to ADA compliant apparatus and other apparatus can be used to practice the invention.

The small mechanical force 62 in combination with the coefficient of friction of the dispensing membrane 48 is enough to break the connection between pre-determined connector 22 (FIG. 3) and/or the grasping tabs 28 (FIG. 4) and/or overcome the coefficient of friction between the first glove 12 and the second glove 12' (FIG. 5) to fully dispense the first glove 12 and advance the cuff end 16' of the second glove 12' into an exposed position in the glove dispensing apparatus 40 for dispensing.

Figure 11:
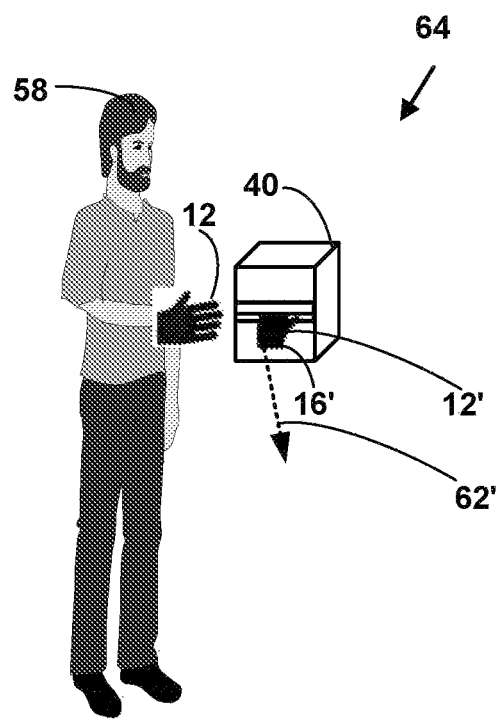
FIG. 11 is a block diagram illustrating the exemplary user of the exemplary protective glove dispensing apparatus of FIG. 10.

FIG. 11 is a block diagram 62 illustrating the exemplary user 58 of the exemplary protective glove dispensing apparatus 40 of FIG. 10 (not drawn to scale). The user 58 in FIG. 11 has dispensed with a first mechanical force 62 and donned the first protective glove 12 by the cuff end 16 and is ready to dispense the second protective glove 12' by the cuff end 16' with another small mechanical force 62'.

The small mechanical force 62 in combination with the coefficient of friction of the dispensing membrane 48 is enough to break the connection between the second protective glove 12' and the third protective 12", fully dispense the second protective glove 12' and also advance the cuff end 16" of the third protective glove into an expose position in the glove dispensing apparatus 40 for dispensing.

The small mechanical forces 62, 62' are used for dispensing protective gloves 12, 12' by the cuff ends 16, 16' when the gloves 12 are stored in a chain 34, stack 36 [ [38]] and/or any other configuration within the glove dispensing apparatus 40.

In addition, the small mechanical forces 62, 62' are used in a similar manner for dispensing protective gloves 12, 12' by the cuff ends 16, 16' when the dispensing slot 44 is on a side surface (FIG. 8) or top surface (FIG. 9) of the glove dispensing apparatus 12.

However, the present inventions is not limited to these embodiments and other embodiments with other combinations of elements can be used to practice the invention.

The drawings included herein illustrate a protective glove 12 extending out of glove dispensing apparatus 40, 40' with a thumb of a finger portion 14 exposed to further illustrate features of the invention. However, in an actual embodiment, only a small portion of the cuff portion 16 of a protective glove 12 is exposed to the surrounding environment.

In another embodiment, the dispensing slot 44 further includes a protective flap 49 (FIG. 8) that protects most of the cuff end 16 of a protective glove 12 from the surrounding environment. However, the present invention is not limited to this embodiment and the invention can be practiced without the protective flap.

In another embodiment, protective gloves 12 are folded one or more times over and around a vertical axis. After the fold, protective gloves are smaller in size when compared with a full size of an unfolded protective glove. The folding allows protective gloves 12, 12' to be stored in smaller protective cases 14 and dispensed from apparatus 40, 40'. The folded protective gloves 12, 12' are still dispensed by the cuff ends 16, 16' and still easily grabbed, unfolded and applied to a user's 58 hands 60, 60'.

In another embodiment, only thumb portions of protective gloves 12, 12' are folded inward around a vertical axis onto the finger portions 14, 14' of the protective gloves. This also allows a chain 34 or stack 36 to be shorter in width. The folded thumbs have minimal effects on the dispensing and donning of protective gloves 12, 12' as they are dispensed by the cuff ends from the apparatus 40, 40'.

Figure 7:
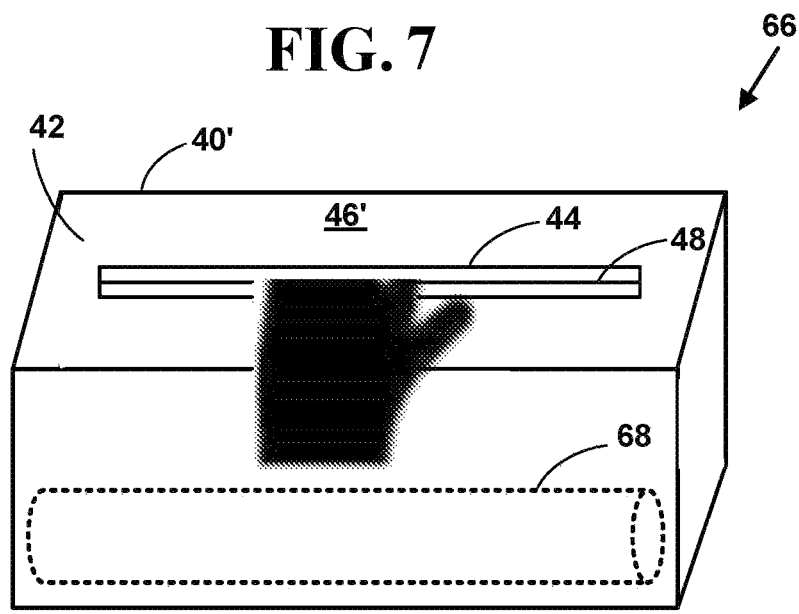
FIG. 7 is a block diagram illustrating an exemplary protective glove dispensing apparatus with a roll of protective gloves.

FIG. 7 is a block diagram 66 illustrating an exemplary protective glove dispensing apparatus with a roll of protective gloves 68.

The roll of protective gloves 68 includes protective gloves 12, 12' rolled onto the roll 68 with the pre-determined overlap 20 and with and/or without pre-determined connector 22 and/or additional grasping tab 28 so protective gloves 12, 12' are dispensed by cuff end 16, 16' from the glove dispensing apparatus 40, 40. The one or more small mechanical forces 62, 62' are applied by the user 58 to rotate the roll 68 within the protective case 14.

Method for Dispensing Protective Gloves

FIG. 12 is a flow diagram illustrating a Method 70 of dispensing protective gloves by cuff ends from the exemplary protective glove dispensing apparatus. At Step 72, a first small mechanical force is applied to a first cuff end of a first protective glove exposed from a sanitary glove dispensing apparatus to fully dispense the first protective glove and expose a second cuff end of a second protective glove, the sanitary glove dispensing apparatus including a plurality of protective gloves connected and stored in a pre-determined storage configuration of protective gloves connected in the pre-determined storage configuration with a pre-determined connector, wherein each of the individual gloves is stored in the pre-determined storage configuration of protective gloves in a pre-determined overlap pattern, wherein protective gloves from the plural protective gloves in the pre-determined storage configuration of protective gloves is dispensed by the cuff ends through a dispensing membrane avoiding contaminating the finger surfaces by a user of the protective gloves during dispensing. At Step 74, a second small mechanical force is applied to the second cuff end of the second protective glove exposed from the sanitary glove dispensing apparatus to fully dispense the second protective glove and expose a third cuff end of a third protective glove.

Method 70 is illustrated with an exemplary embodiment. However, the present invention is not limited to this exemplary embodiment and other embodiments can be used to practice the invention.

In such an exemplary embodiment at Step 72, a first small mechanical force 62 is applied to a first cuff end 16 of a first protective glove 12 exposed from a sanitary glove dispensing apparatus 40, 40' to fully dispense the first protective glove 12 and expose a second cuff end 16' of a second protective glove 12' protective gloves 12, 12', the sanitary glove dispensing apparatus 40, 40' including plurality of protective gloves 12 connected and stored in a pre-determined storage configuration, including, but not limited to, a chain 34, stack 36 and/or roll 68 of protective gloves 12 including a plurality of protective gloves 12 connected in the pre-determined storage configuration 34, 36, 68 with a pre-determined connector 22, wherein each of the individual gloves 12 in the pair of protective gloves is stored in the pre-determined storage configuration of protective gloves in a pre-determined overlap pattern 20, wherein protective gloves from the plural protective gloves in the pre-determined storage configuration of protective gloves is dispensed by the cuff ends 16, 16'. through a dispensing membrane avoiding contaminating the finger surfaces 14, 14' by a user 58 of the protective gloves during dispensing.

At Step 72, a second small mechanical force 62' is applied to the second cuff end 14' of the second protective glove 12' exposed from the sanitary glove dispensing apparatus 40, 40' to fully dispense the second protective glove 12' and expose a third cuff end 16" of a third protective glove 12".

The embodiments described herein dispense protective gloves 12, 12' by the cuff ends 16, 16' and prevent contamination of the finger surface 14, 14' of the protective gloves. The present invention helps to dramatically decrease transfer of pathogenic organisms by health care and food service workers.

The embodiments of the claimed invention described herein dispenses protective gloves 12, 12' in a way that is in stark contrast to boxes of protective gloves or other mechanical glove dispensers known in the prior art. Protective gloves stored in such prior art boxes are stored in random clumps of gloves in random orientations in which the protective gloves 12, 12' can be extracted from the glove box by the finger ends 14 instead of the cuff 16 end and in which multiple gloves can and are normally and typically removed from the box, touched and contaminated by one or more users and even put back into the box after being contaminated by plural users to further contaminate the remaining gloves in the glove box. In the glove dispensers known in the art, once a first protective glove is dispensed, a portion of other finger ends of protective gloves in the box are constantly exposed to the environment allowing that protective glove or gloves to be continually touched and contaminated by the external environment to which the protective gloves are exposed.

Presented herein is a sanitary glove dispensing apparatus. The sanitary glove dispensing apparatus, dispenses connected protective gloves overlapped in a pre-determined pattern, by both cuff ends, so finger ends of the protective gloves are not contaminated during dispensing and protecting remaining protective gloves in the apparatus from surrounding environment and from other users of the apparatus.

It should be understood that the architecture, programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

While various elements of the preferred embodiments have been described as being implemented in software, in other embodiments hardware or firmware implementations may alternatively be used, and vice-versa.

The claims should not be read as limited to the described order or elements unless stated to that effect. In addition, use of the term "means" in any claim is intended to invoke 35 U.S.C. § 112, paragraph 6, and any claim without the word "means" is not so intended. Therefore, all embodiments that come within the scope and spirit of the following claims and equivalents thereto are claimed as the invention.

I claim:

1. A dispenser for sanitary polymeric gloves, each of which includes two opposite surfaces with a cuff-end portion, a palm portion and a finger-end portion, comprising:
    a protective case including a dispensing slit; and
    a plurality of unfolded gloves disposed in succession into a linear unfolded chain rolled into a roll disposed within the case such that an axis of rotation of the roll is along the dispensing slit, the finger-end portion of each glove overlapping the cuff-end portion of the succeeding glove with a friction-only connection between the overlapping polymeric surfaces of adjacent gloves being such that pulling the cuff-end portion of a slit-adjacent glove rotates the roll within the protective case to unroll the chain, causing cuff-first dispensing through the slit of the slit-adjacent glove and breaking its finger-end-portion friction-only connection to the cuff-end portion of the succeeding glove in the chain, thereby leaving at least the finger-end portion of the succeeding glove within the protective case and exposing its cuff-end portion for later dispensing purposes.

2. The dispenser of claim 1 wherein the gloves include medical gloves, food service gloves and other types of protective gloves.

3. The dispenser of claim 1 wherein the polymeric gloves are of a material selected from the group consisting of latex, nitrile rubber, vinyl, neoprene and polyethylene.

4. The dispenser of claim 1 wherein the dispensing slit further includes a dispensing membrane coated with an antimicrobial compound to provide additional protection of gloves dispensed from the apparatus.

5. The dispenser of claim 1 wherein an overlap distance between adjacent protective gloves is about four inches (about ten centimeters).

6. A dispenser for sanitary polymeric gloves, each of which includes two opposite surfaces with a cuff-end portion, a palm portion and a finger-end portion, comprising:
    a protective case including a dispensing slit; and
    a plurality of unfolded gloves disposed in succession into a linear unfolded chain rolled into a roll disposed within the case such that an axis of rotation of the roll is along the dispensing slit, the finger-end portion of each glove overlapping the cuff-end portion of the succeeding glove and having a connector forming a connection therebetween, the connection being such that pulling the cuff-end portion of a slit-adjacent glove rotates the roll within the protective case to unroll the chain, causing cuff-first dispensing through the slit of a slit-adjacent glove and breaking its finger-end-portion connection to the cuff-end portion of the succeeding glove in the chain, thereby leaving at least the finger-end portion of the succeeding glove within the protective case and exposing its cuff-end portion for later dispensing purposes.

7. The dispenser of claim 6 wherein the connector is one of a chemical, heat or mechanical compression bond.

8. The dispenser of claim 6 wherein the connector is a chemical bond which includes a pressure sensitive adhesive (PSA).

* * * * *